(12) United States Patent
Modak et al.

(10) Patent No.: US 7,759,327 B2
(45) Date of Patent: Jul. 20, 2010

(54) COMPOSITIONS CONTAINING ZINC SALTS FOR COATING MEDICAL ARTICLES

(75) Inventors: Shanta M. Modak, River Edge, NJ (US); Luserpina Caraos, New York, NY (US); Carlo Micceri, Katonah, NY (US)

(73) Assignees: The Trustees of Columbia University in the City of New York, New York, NY (US); VSP Technologies, Inc., Ossining, NY (US)

( * ) Notice: Subject to any disclaimer, the term of this patent is extended or adjusted under 35 U.S.C. 154(b) by 932 days.

(21) Appl. No.: 11/446,347

(22) Filed: Jun. 2, 2006

(65) Prior Publication Data

US 2009/0035390 A1     Feb. 5, 2009

Related U.S. Application Data

(63) Continuation-in-part of application No. 11/327,677, filed on Jan. 6, 2006.

(51) Int. Cl.
*A61K 31/60* (2006.01)
*A61K 31/315* (2006.01)
*A61K 33/32* (2006.01)

(52) U.S. Cl. ................ 514/159; 514/494; 424/641; 424/642

(58) Field of Classification Search ............... 514/159, 514/494; 424/641, 642
See application file for complete search history.

(56) References Cited

U.S. PATENT DOCUMENTS

| | | |
|---|---|---|
| 3,257,276 A | 6/1966 | Broh-Kahn et al. |
| 3,485,915 A | 12/1969 | Gerstien et al. |
| 3,960,745 A | 6/1976 | Billany et al. |
| 4,243,657 A | 1/1981 | Okumura et al. |
| 4,393,076 A | 7/1983 | Noda et al. |
| 4,478,853 A | 10/1984 | Chaussee et al. |
| 4,587,266 A | 5/1986 | Verdicchio |
| 4,604,384 A | 8/1986 | Smith et al. |
| 4,853,978 A | 8/1989 | Stockum |
| 4,868,169 A | 9/1989 | O'Laughlin et al. |
| 4,870,108 A | 9/1989 | Page |
| 4,889,844 A | 12/1989 | Silvetti, Sr. et al. |
| 4,910,205 A | 3/1990 | Kogan et al. |
| 4,919,837 A | 4/1990 | Gluck |
| 4,956,170 A | 9/1990 | Lee et al. |
| 4,963,591 A | 10/1990 | Fourman et al. |
| 5,031,245 A | 7/1991 | Milner |
| 5,059,416 A | 10/1991 | Cherukuri et al. |
| 5,073,372 A | 12/1991 | Turner et al. |
| 5,089,205 A | 2/1992 | Huang et al. |
| 5,110,809 A | 5/1992 | Wang et al. |
| 5,116,602 A | 5/1992 | Robinson et al. |
| 5,133,090 A | 7/1992 | Modak et al. |
| 5,147,648 A | 9/1992 | Bannert |
| 5,164,107 A | 11/1992 | Khan et al. |
| 5,208,031 A | 5/1993 | Kelly |
| 5,357,636 A | 10/1994 | Dresdner, Jr. et al. |
| 5,403,864 A | 4/1995 | Bruch et al. |
| 5,447,930 A | 9/1995 | Nayak |
| 5,516,510 A | 5/1996 | Beilfuss et al. |
| 5,591,442 A | 1/1997 | Diehl et al. |
| 5,599,549 A | 2/1997 | Wivell et al. |
| 5,612,324 A | 3/1997 | Guang Lin et al. |
| 5,624,675 A | 4/1997 | Kelly |
| 5,624,962 A | 4/1997 | Takeuchi et al. |
| 5,658,575 A | 8/1997 | Ribier et al. |
| 5,705,532 A | 1/1998 | Modak et al. |
| 5,708,023 A | 1/1998 | Modak et al. |
| 5,736,574 A | 4/1998 | Burnier et al. |
| 5,750,122 A | 5/1998 | Evans et al. |
| 5,753,270 A | 5/1998 | Beauchamp et al. |
| 5,763,412 A | 6/1998 | Khan et al. |
| 5,776,430 A | 7/1998 | Osborne et al. |
| 5,804,203 A | 9/1998 | Hahn et al. |
| 5,830,488 A | 11/1998 | Suzuki et al. |
| 5,885,562 A | 3/1999 | Lowry |
| 5,902,572 A | 5/1999 | Luebbe et al. |
| 5,906,808 A | 5/1999 | Osborne et al. |
| 5,951,993 A | 9/1999 | Scholz et al. |
| 5,965,132 A | 10/1999 | Thorpe et al. |
| 5,965,610 A | 10/1999 | Modak et al. |
| 5,980,477 A | 11/1999 | Kelly |
| 5,980,925 A | 11/1999 | Jampani et al. |

(Continued)

FOREIGN PATENT DOCUMENTS

DE     4140474     6/1993

(Continued)

OTHER PUBLICATIONS

Modak et al. (2005). "A topical cream containing a zinc gel (allergy guard) as a prophylactic against latex glove-related contact dermatitis", Dermatitis. 16(1): 22-7.

(Continued)

*Primary Examiner*—Raymond J Henley, III
(74) *Attorney, Agent, or Firm*—Baker Botts L.L.P.

(57) ABSTRACT

The present invention relates to methods and compositions which employ low concentrations of combinations of zinc salts and antimicrobial agents in coatings for medical articles. The coatings have an anti-irritant effect and inhibit transmission of infectious disease.

4 Claims, No Drawings

U.S. PATENT DOCUMENTS

| | | | |
|---|---|---|---|
| 5,985,918 A | 11/1999 | Modak et al. |
| 5,985,931 A | 11/1999 | Modak et al. |
| 6,022,551 A | 2/2000 | Jampani et al. |
| 6,037,386 A | 3/2000 | Modak et al. |
| 6,040,347 A | 3/2000 | Cupferman et al. |
| 6,045,817 A | 4/2000 | Ananthapadmanabhan et al. |
| 6,107,261 A | 8/2000 | Taylor et al. |
| 6,110,908 A | 8/2000 | Guthery |
| 6,136,771 A | 10/2000 | Taylor et al. |
| 6,183,766 B1 | 2/2001 | Sine et al. |
| 6,187,327 B1 | 2/2001 | Stack |
| 6,204,230 B1 | 3/2001 | Taylor et al. |
| 6,211,243 B1 | 4/2001 | Johnson |
| 6,248,343 B1 | 6/2001 | Jampani et al. |
| 6,287,583 B1 | 9/2001 | Warren et al. |
| 6,294,186 B1 | 9/2001 | Beerse et al. |
| 6,319,958 B1 | 11/2001 | Johnson et al. |
| 6,321,750 B1 | 11/2001 | Kelly |
| 6,323,171 B1 | 11/2001 | Fonsny et al. |
| 6,344,218 B1 | 2/2002 | Dodd et al. |
| 6,352,701 B1 | 3/2002 | Scholz et al. |
| 6,376,522 B1 | 4/2002 | Holzl et al. |
| 6,387,357 B1 | 5/2002 | Chopra et al. |
| 6,403,067 B1 | 6/2002 | Schamper et al. |
| 6,403,071 B1 | 6/2002 | Scavone et al. |
| 6,414,032 B1 | 7/2002 | Johnson |
| 6,420,431 B1 | 7/2002 | Johnson |
| 6,426,062 B1 | 7/2002 | Chopra et al. |
| 6,511,657 B2 | 1/2003 | Avendano et al. |
| 6,582,711 B1 | 6/2003 | Asmus et al. |
| 6,613,312 B2 | 9/2003 | Rizvi et al. |
| 6,682,749 B1 | 1/2004 | Potechin et al. |
| 6,723,689 B1 | 4/2004 | Hoang et al. |
| 6,846,846 B2 | 1/2005 | Modak et al. |
| 7,435,429 B2 * | 10/2008 | Modak et al. ............... 424/641 |
| 7,563,461 B2 * | 7/2009 | Modak et al. ............... 424/641 |
| 2002/0022660 A1 | 2/2002 | Jampani et al. |
| 2002/0098159 A1 | 7/2002 | Wei et al. |
| 2002/0165130 A1 | 11/2002 | Johnson et al. |
| 2003/0152644 A1 | 8/2003 | Modak et al. |
| 2003/0157138 A1 | 8/2003 | Eini et al. |
| 2003/0211066 A1 | 11/2003 | Scholz et al. |
| 2004/0102429 A1 | 5/2004 | Modak et al. |
| 2004/0208908 A1 | 10/2004 | Modak et al. |
| 2004/0253275 A1 | 12/2004 | Eini et al. |
| 2005/0019431 A1 | 1/2005 | Modak et al. |
| 2005/0048139 A1 | 3/2005 | Modak et al. |
| 2005/0238602 A1 | 10/2005 | Modak et al. |
| 2005/0281762 A1 | 12/2005 | Modak et al. |
| 2006/0141017 A1 | 6/2006 | Kling et al. |

FOREIGN PATENT DOCUMENTS

| | | |
|---|---|---|
| DE | 4240674 | 3/1994 |
| DE | 19523320 | 1/1997 |
| EP | 0041448 | 12/1981 |
| EP | 304802 | 3/1989 |
| EP | 402078 | 9/1992 |
| EP | 0521455 | 1/1993 |
| EP | 0604848 | 7/1994 |
| EP | 0674896 | 10/1995 |
| EP | 0694310 | 1/1996 |
| EP | 0313302 | 4/1998 |
| EP | 1001012 | 5/2000 |
| FR | 2729050 | 7/1996 |
| JP | 10328284 | 12/1998 |
| RU | 2166309 | 5/2001 |
| SU | 833240 | 5/1981 |
| WO | WO8400111 | 1/1984 |
| WO | WO8704350 | 7/1987 |
| WO | WO8800795 | 2/1988 |
| WO | WO8803799 | 6/1988 |
| WO | WO8905645 | 6/1989 |
| WO | WO9307903 | 4/1993 |
| WO | WO9318745 | 9/1993 |
| WO | WO9318852 | 9/1993 |
| WO | WO9415461 | 7/1994 |
| WO | WO 94/18939 | 9/1994 |
| WO | WO9526134 | 10/1995 |
| WO | WO9824426 | 6/1998 |
| WO | WO9851275 | 11/1998 |
| WO | WO9903463 | 1/1999 |
| WO | WO99/38505 | 5/1999 |
| WO | WO9938505 | 8/1999 |
| WO | WO9960852 | 12/1999 |
| WO | WO9963816 | 12/1999 |
| WO | WO0037042 | 6/2000 |
| WO | WO0141573 | 6/2001 |
| WO | WO03003896 | 1/2003 |
| WO | WO 03/034994 | 5/2003 |
| WO | WO03034994 | 5/2003 |
| WO | WO 03/066001 | 8/2003 |
| WO | WO 03/066001 A2 | 8/2003 |
| WO | WO03083028 | 10/2003 |
| WO | WO2004014416 | 2/2004 |
| WO | WO2006099359 | 9/2006 |
| WO | WO2007069214 | 6/2007 |

OTHER PUBLICATIONS

Cimiotti et al. (2003). "Adverse reactions associated with an alcohol-based hand antiseptic among nurses in a neonatal intensive care unit", Am. J. Infect. Control 31: 43-48.

Bleasel et al. (2002). "Allergic contact dermatitis following exposure to essential oils", Australian Journal of Dermatology 43: 211-213.

Vilaplana et al. (2002). "Contact dermatitis from the essential oil of tangerine in fragrances", Contact Dermatitis 46: 108.

Larsen et al. (2001). "Fragrance contact dermatitis: a worldwide multicenter investigation (Part II)", Contact Dermatitis 44: 344-346.

Nair. (2001). "Final report on the safety assessment of *Mentha piperita* (Peppermint) oil, *Mentha piperita* (Peppermint) Leaf extract, *Mentha piperita* (Peppermint) leaf and *Mentha piperita* (Peppermint) water", International Journal of Toxicology 20 (Suppl 3): 61-73.

Wohrl. (2001). "The significance of fragrance mix, balsam of Peru, colophony and propolis as screening tools in the detection of fragrance allergy", British Journal of Dermatology 145(2): 268-273.

Sugiura. (2000). "Results of patch testing with lavender oils in Japan", Contact Dermatitis 43: 157-160.

De Groot et al. (1997). "Adverse reactions to fragrances: a clinical review", Contact Dermatitis 36: 57-86.

Modak et al. (1997). A Topical Zinc Gluconate Gel Composition for the Prevention of latex/Starch Glove Related Allergic Reactions: Pilot Study in Volunteers. In: Programs and Abstracts of the 37th Interscience Conference on Antimicrobial Agents and Chemotherapy, Toronto; American Society for Microbiology Washington DC. Abstract J -52.

Goodman and Gilman's The Pharmacological Basis of Therapeutics (Goodman Gilman A, Rall TW, Nies AS, Taylor P, ed. (Pergamon Press; Elmsford, N.Y.: 1990).

Bush et al. (1986). "Pig skin as test substrate for evaluating topical antimicrobial activity", J. Clin. Microbiol. 24: 343-348.

Meyer et al. (1978). "The skin of domestic mammals as a model for the human skin, with special reference to the domestic pig", Curr. Problem. Dematol. 7: 39-52.

Lansdown, "Interspecies variations in response to topical application of selected zinc compounds," Food Chem Toxicol. Jan. 1991;29(1):57-64.

Rosenthal, S.L.; Effect of Medicaments on the Motility of the Oral Flora with Special Reference to the Treatment of Vincent's Infection; II. Journal of Dental Research; 1943; vol. 22, pp. 491-494.

U.S. Appl. No. 10/622,272, filed Jul. 17, 2003.

U.S. Appl. No. 11/031,258, filed Jan. 7, 2005.

U.S. Appl. No. 11/143,012, filed Jun. 2, 2005.

U.S. Appl. No. 11/327,677, filed Jan. 6, 2006.
U.S. Appl. No. 10/892,034, filed Jul. 15, 2004.
U.S. Appl. No. 10/891,624, filed Jul. 15, 2004.
U.S. Appl. No. 08/492,080, filed Jun. 28, 1995.
U.S. Appl. No. 08/760,054, filed Dec. 4, 1996.
U.S. Appl. No. 08/871,071, filed Jun. 9, 1997.
U.S. Appl. No. 09/387,550, filed Aug. 31, 1999.
U.S. Appl. No. 10/047,631, filed Oct. 23, 2001.
U.S. Appl. No. 10/785,207, filed Feb. 24, 2004.
U.S. Appl. No. 10/786,681, filed Feb. 25, 2004.
U.S. Appl. No. 08/218,666, filed Mar. 28, 1994.
U.S. Appl. No. 10/622,272, Apr. 13, 2007 Non-Final Office Action.
U.S. Appl. No. 10/622,272, Oct. 15, 2007 Response to Non-Final Office Action.
U.S. Appl. No. 10/622,272, Jan. 30, 2008 Non-Final Office Action.
U.S. Appl. No. 10/622,272, Apr. 28, 2008 Response to Non-Final Office Action.
U.S. Appl. No. 10/622,272, Jul. 4, 2008 Final Office Action.
U.S. Appl. No. 10/622,272, Nov. 21, 2008 Response to Final Office Action.
U.S. Appl. No. 10/622,272, Jan. 22, 2009 Non-Final Office Action.
U.S. Appl. No. 10/622,272, Apr. 22, 2009 Response to Non-Final Office Action.
U.S. Appl. No. 10/622,272, Jul. 2, 2009 Final Office Action.
U.S. Appl. No. 10/622,272, Sep. 29, 2009 Response to Final Office Action.
U.S. Appl. No. 10/622,272, Dec. 21, 2009 Non-Final Office Action.
U.S. Appl. No. 10/785,207, Nov. 19, 2007 Non-Final Office Action.
U.S. Appl. No. 10/785,207, Feb. 19, 2008 Response to Non-Final Office Action.
U.S. Appl. No. 10/785,207, May 14, 2008 Final Office Action.
U.S. Appl. No. 10/785,207, Aug. 13, 2008 Response to Final Office Action.
U.S. Appl. No. 10/785,207, Sep. 22, 2008 Non-Final Office Action.
U.S. Appl. No. 10/785,207, Dec. 18, 2008 Response to Non-Final Office Action.
U.S. Appl. No. 10/785,207, Mar. 5, 2009 Final Office Action.
U.S. Appl. No. 10/785,207, May 28, 2009 Response to Final Office Action.
U.S. Appl. No. 10/785,207, Aug. 11, 2009 Non-Final Office Action.
U.S. Appl. No. 10/785,207, Nov. 2, 2009 Response to Non-Final Office Action.
U.S. Appl. No. 10/786,681, May 21, 2007 Non-Final Office Action.
U.S. Appl. No. 10/786,681, Sep. 6, 2007 Response to Non-Final Office Action.
U.S. Appl. No. 10/786,681, Nov. 21, 2007 Final Office Action.
U.S. Appl. No. 10/786,681, Feb. 21, 2008 Response to Final Office Action.
U.S. Appl. No. 10/786,681, Jul. 7, 2008 Non-Final Office Action.
U.S. Appl. No. 10/786,681, Oct. 2, 2008 Response to Non-Final Office Action.
U.S. Appl. No. 10/786,681, Dec. 23, 2008 Final Office Action.
U.S. Appl. No. 10/786,681, Mar. 23, 2009 Response to Final Office Action.
U.S. Appl. No. 10/786,681, May 27, 2009 Non-Final Office Action.
U.S. Appl. No. 10/786,681, Aug. 27, 2009 Response to Non-Final Office Action.
U.S. Appl. No. 10/786,681, Nov. 24, 2009 Final Office Action.
U.S. Appl. No. 10/891,624, Apr. 10, 2007 Non-Final Office Action.
U.S. Appl. No. 10/891,624, Oct. 3, 2007 Response to Non-Final Office Action.
U.S. Appl. No. 10/891,624, Dec. 18, 2007 Final Office Action.
U.S. Appl. No. 10/891,624, Apr. 7, 2008 Response to Final Office Action.
U.S. Appl. No. 10/891,624, Jul. 24, 2008 Non-Final Office Action.
U.S. Appl. No. 10/891,624, Oct. 22, 2008 Response to Non-Final Office Action.
U.S. Appl. No. 10/891,624, Jan. 26, 2009 Final Office Action.
U.S. Appl. No. 10/891,624, Apr. 23, 2009 Response to Final Office Action.
U.S. Appl. No. 10/891,624, Aug. 6, 2009 Non-Final Office Action.
U.S. Appl. No. 10/891,624, Nov. 4, 2009 Response to Non-Final Office Action.
U.S. Appl. No. 11/327,677, Jun. 1, 2009 Non-Final Office Action.
U.S. Appl. No. 11/327,677, Aug. 27, 2009 Response to Non-final Office Action.
U.S. Appl. No. 11/327,677, Nov. 2, 2009 Notice of Allowance.
U.S. Appl. No. 11/143,012, Oct. 31, 2008 Non-Final Office Action.
U.S. Appl. No. 11/143,012, Jan. 16, 2009 Response to Non-Final Office Action.
U.S. Appl. No. 11/143,012, Mar. 24, 2009 Notice of Allowance.
U.S. Appl. No. 11/031,258, Jun. 6, 2007 Non-Final Office Action.
U.S. Appl. No. 11/031,258, Aug. 22, 2007 Response to Non-Final Office Action.
U.S. Appl. No. 11/031,258, Dec. 6, 2007 Notice of Allowance.
U.S. Appl. No. 10/047,631, Nov. 14, 2003 Non-Final Office Action.
U.S. Appl. No. 10/047,631, Apr. 16, 2004 Response to Non-Final Office Action.
U.S. Appl. No. 10/047,631, Jul. 12, 2004 Notice of Allowance.
U.S. Appl. No. 10/892,034, Jan. 29, 2008 Non-Final Office Action.
U.S. Appl. No. 10/892,034, Jun. 17, 2008 Response to Non-Final Office Action.
U.S. Appl. No. 10/892,034, Aug. 27, 2008 Final Office Action.
U.S. Appl. No. 10/892,034, Jan. 27, 2009 Response to Final Office Action.
U.S. Appl. No. 10/892,034, Apr. 8, 2009 Non-Final Office Action.
U.S. Appl. No. 10/892,034, Jul. 2, 2009 Response to Non-Final Office Action.
U.S. Appl. No. 10/892,034, Oct. 9, 2009 Final Office Action.
U.S. Appl. No. 08/492,080, Sep. 13, 1996 Non-Final Office Action.
U.S. Appl. No. 08/492,080, Jan. 13, 1997 Response to Non-Final Office Action.
U.S. Appl. No. 08/492,080, Apr. 19, 1997 Final Office Action.
U.S. Appl. No. 08/492,080, Jul. 9, 1997 Response to Final Office Action.
U.S. Appl. No. 08/492,080, Aug. 5, 1997 Examiner Interview Summary Record.
U.S. Appl. No. 08/492,080, Aug. 6, 1997 Notice of Allowance.
U.S. Appl. No. 08/760,054, Mar. 28, 1997 Non-Final Office Action.
U.S. Appl. No. 08/760,054, Jul. 28, 1997 Response to Non-Final Office Action.
U.S. Appl. No. 08/760,054, Nov. 19, 1997 Final Office Action.
U.S. Appl. No. 08/760,054, Apr. 17, 1998 Notice of Appeal Filed.
U.S. Appl. No. 08/760,054, Apr. 17, 1998 Amendment/Argument after Notice of Appeal.
U.S. Appl. No. 08/760,054, May 15, 1998 Advisory Action.
U.S. Appl. No. 08/760,054, Aug. 17, 1998 Express Abandonment.
U.S. Appl. No. 08/760,054, Aug. 17, 1998 Continuing Prosecution Application—Continuation (ACPA).
U.S. Appl. No. 08/760,054, Nov. 24, 1998 Non-Final Office Action.
U.S. Appl. No. 08/760,054, Mar. 17, 1999 Response to Non-Final Office Action.
U.S. Appl. No. 08/760,054, Jun. 18, 1999 Examiner's Amendment.
U.S. Appl. No. 08/760,054, Jun. 21, 1999 Notice of Allowance.
U.S. Appl. No. 08/871,071, May 8, 1998 Non-Final Office Action.
U.S. Appl. No. 08/871,071, Nov. 9, 1998 Response to Non-Final Office Action.
U.S. Appl. No. 08/871,071, Dec. 9, 1998 Terminal Disclaimer Approved.
U.S. Appl. No. 08/871,071, Dec. 16, 1998 Non-Final Office Action.
U.S. Appl. No. 08/871,071, Mar. 19, 1999 Response to Non-Final Office Action.
U.S. Appl. No. 08/871,071, Apr. 16, 1999 Notice of Allowance.
U.S. Appl. No. 09/387,550, Nov. 9, 1999 Notice of Allowance.
U.S. Appl. No. 09/387,550, Nov. 4, 2005 Certificate of Correction.
U.S. Appl. No. 09/387,550, Nov. 22, 2005 Certificate of Correction.
U.S. Appl. No. 08/218,666, Mar. 3, 1995 Non-Final Office Action.
U.S. Appl. No. 08/218,666, Sep. 7, 1995 Response to Non-Final Office Action.
U.S. Appl. No. 08/218,666, Dec. 18, 1995 Final Office Action.
3M Avagard Surgical and Healthcare Personnel Hand Antiseptic with Moisturizers news release, 3M Company, Jun. 11, 2001.
3M Avagard Surgical and Healthcare Personnel Hand Antiseptic with Moisturizers product description, 3M Company, 2001.
A-Z of exhibitors; at Central European Coatings Show, PPC1. Polymers Paint Colour Journal, No. 4433, vol. 190, p. 42, Oct. 1, 2000.

Beilfuss, "A multifunctional ingredient for deodorants," SOFW Journal, 1998, vol. 124, p. 360, 362-364, 366.

Bezic et al., 2003, "Composition and antimicrobial activity of *Achillea clavennae* L. essential oil." Phytother. Res. 17(9):1037-1040.

Brehm-Stecher et al. 2003, "Sensitization of *Staphylococcus aureus* and *Escherichia coli* to antibiotics by the sesquiterpenoids nerolidol, farnesol, bisabolol, and apritone." Antimicrobial Agents and Chemotherapy, 47(10):3357-3360.

de Abreu Gonzaga et al., "Composition and antibacterial activity of the essential oils from *Zanthoxylum rhoifolium*." 2003, Planta Med. 69(8):773-775.

"Drug Information for the Health Care Professional," vol. 1A, USP-DI, 1989, Ninth Edition, pp. 792-793, Banta Company, VIR.

Fitzgerald, K.A., Davies, A., and Russel, A.D., "Mechanism of Action of Chlorhexidine Diacitate and Phenoxyethanol Singly and in Combination Against Gram-negative Bacteria," 215 Mibrobio 70:215-229 (1992).

"Fraicheur de Peau Fresh Skin Body Mist," International Product Alert, No. 9, vol. 14, May 5, 1997.

Garcia et al., 2003, "Virucidal activity of essential oils from aromatic plants of San Luis, Argentina." Phytother. Res. 17(9):1073-1075.

Goren et al., 2003, "Analysis of essential oil of *Coridothymus capitatus* (L.) and its antibacterial and antifungal activity." Z. Naturforsch. 58(9-10):687-690.

Hajhashemi et al., 2003, "Anti-inflammatory and analgesic properties of the leaf extracts and essential oil of *Lavandula angustifolia* Mill." Ethnopharmacol. 89(1 ):67-71.

Happi, Household & Personal Products Industry: New ingredients galore at SCC supplier's day, Chemical Business Newsbase, Aug. 1, 2000.

Heard, D.D., and Ashworth, R.W., "The Colloidal Properties of Chlorhexidine and its Interaction with Some Macromolecules," J. Pharm. Pharmac. 20:505-12, 1968.

Lawless, Julia. The Illustrated Encyclopedia of Essential Oils: The Complete Guide to the Use of Oils in Aromatherapy and Herbalism. Element Books, 1995, USA. pp. 132,162-164,169,223,227 and 228.

Lawrence, J.C. et al., "Evaluation of Phenoxeotol—Chlorhexidine Cream as a Prophylactic Antibacterial Agent in Burns," The Lancet, pp. 1037-1040, May 8, 1992.

Manufacturing Chemist: Japan approve Schulke & Mayr's Sensiva SC 50, Chemical Business Newsbase, Jul. 14, 2000.

Minami et al., 2003, "The inhibitory effect of essential oils on herpes simplex virus type-1 replication in vitro." Microbial Immunol. 47(a):681-684.

Modak S. et al., "Rapid Inactivation of Infections Pathogess by Chlorhexidine Coated Gloves," Infection Control and Hospital Epidemiology, 13:463-471, (1992).

Molnycke Healthcare "Hibiclens Antiseptic/Antimicrobial Skin Cleanser" Nov. 10, 2006.

Paranagama et al., 2003, "Fungicidal and anti-aflatoxigenic effects of the essential oil of *Cymbopogon citratus* (DC.) Stapf. (lemongrass) against *Aspergillus flavus* Linle isolated from stored rice." Lett. Appi. Microbiol. 37(1):86-90.

Parfums, Cosmetiques, Aromes: Japan approves sale of new cosmetics ingredient, Chemical Business Newsbase, Jan. 16, 2001.

Physicians Desk Reference—39th Edition, 1985, p. 1858, Lotrisone.

Physicians Desk Reference—39th Edition, 1985, pp. 2037-2038, chlorhexidine.

Physicians Desk Reference—40th Edition, 1986, pp. 1781-1782, chlorhexidine.

Pfizer "Purell Instant Hand Sanitzer, Product Description" Nov. 10, 2006.

Prevacare: Antimicrobial Hand Gel product description, Johnson & Johnson, Advanced Wound Care, 2001.

Prevcare: Total solution skin care spray product description, Johnson & Johnson, Advanced Wound Care, 2001.

Robinson, K. "Heat beating technology; deodorant market," Soap Perfumery and Cosmetics, v. 69 No. 7 p. 34, Jul. 1996.

Rubbo et al., A Review of Sterilization and Disinfection, Year Book Medical Publishers, Chicago, 161-162 (1965).

S &M in Japan—Schulke & Mayr's Sensiva SC 50 deodorant active ingredient received approval for use in the Japanese market, SPC Asia No. 21, p. 35, May 2000.

Schmolka, I.R., "The Synergistic Effects of Nonionic Surfactants Upon Cationic Germicidal Agents," J. Soc. Cosmet. Chem., 24:577-592, 1973.

Schuhmacher et al., 2003, "Virucidal effect of peppermint oil on the enveloped viruses herpes simplex virus type 1 and type 2 in vitro." Phytomedicine 10:504-510.

Schwarzkopf: Moving into a new era, European Cosmetic Markets, Sep. 1, 1996.

Schwarzkopf cares, European Cosmetic Markets, No. 5, vol. 13, May 1, 1996.

Sensiva SC 50 product description from manufacturer website (www.schuelkemayr.com), Schulke & Mayr, manufacturer, printed Apr. 4, 2001.

Shin, 2003, "Anti-*Aspergillus* activities of plant essential oils and their combination effects with ketoconazole or amphotericin B." Arch. Pharm. Res. 26(5):389-393.

Silva et al., 2003, "Analgesic and anti-inflammatory effects of essential oils of *Eucalyptus*." Ethnopharmacoi. 89(2-3);277-283.

SPC, Soap Perfumery and Cosmetics; New for deodorants: Sensiva SC 50, Chemical Business Newsbase, Aug. 12, 1999.

Valero and Salmera, 2003, "Antibacterial activity of 11 essential oils against *Bacillus cereus* in tyndallized carrot broth." Int. Food Microbiol. 85(1-2): 73-81.

Velluti et al., 2003, "Inhibitory effect of cinnamon, clove, lemongrass, oregano and palmarose essential oils on growth and fumonisin B1 production by *Fusarium proliferatum* in maize grain." Int. Food Microbiol. 89: 145-154.

Vichy launches oil-free moisturizer, Chemist & Druggist, p. 792, Jun. 8, 1996.

Woodruff,1. "Mixed feelings," Soap Perfumery & Cosmetics, No. 9, vol. 73, p. 39, Sep. 1, 2000.

* cited by examiner

COMPOSITIONS CONTAINING ZINC SALTS FOR COATING MEDICAL ARTICLES

CROSS REFERENCE TO RELATED APPLICATIONS

The present invention is a continuation-in-part of U.S. patent application Ser. No. 11/327,677, filed Jan. 6, 2006, which is incorporated by reference in its entirety herein.

1. INTRODUCTION

The present invention relates to methods and compositions which employ low concentrations of combinations of zinc salts and antimicrobial agents in coatings for articles such as medical articles. The coatings have an anti-irritant effect and inhibit transmission of infectious disease.

2. BACKGROUND OF THE INVENTION

The Center for Disease Control (CDC) estimates that hospital-acquired infections cost the U.S. healthcare system $4.5 billion a year, and that 80% of these infections are transmitted by direct touch. The emollient solvent octoxyglycerin ("Sensiva") has been found to demonstrate antimicrobial activity, especially in the presence of quaternary ammonium compound and an additional antimicrobial agent, an activity utilized in hand sanitizer formulations (see U.S. Pat. No. 6,846, 846). In addition to or as an alternative to antimicrobial topical formulations, gloves are used by health care practitioners and in other sectors, such as the food service industry, as a means of preventing spread of infection. However, many persons have or develop sensitivities to gloves, including allergic reactions to latex or dermatologic reactions to moisture retention.

It has been recognized that zinc salts can inhibit irritation caused by a variety of agents. See for example, U.S. Pat. Nos. 5,708,023, 5,965,610, 6,037,386, and 5,985,918. These patents teach the use of relatively high concentrations of zinc, which might be detrimental if taken internally.

3. SUMMARY OF THE INVENTION

The present invention relates to articles, especially medical articles, coated with combinations of two or more water-soluble zinc salts and one or more antimicrobial agent. Such coating may further comprise agents such as an emollient solvent, an essential oil or component thereof, and/or a silicone powder. Articles which may be coated according to the invention include, but are not limited to, gloves, male and female condoms, medical clothing, bandages, footwear, etc. The coating of the invention enhances the protective value of the article while inhibiting irritation of skin coming in contact with the article.

4. DETAILED DESCRIPTION OF THE INVENTION

The present invention relates, at least in part, to methods and compositions for coating articles, especially medical articles, which, in the case of barrier medical articles and medical articles which come in contact with the skin or mucous membranes, respectively, improve the effectiveness of the barriers in preventing the transmission of infectious disease and decrease skin and/or mucosal irritation caused by the article.

In various embodiments, the present invention provides for the use of low concentrations of water soluble zinc salts and one or more antimicrobial agent, in coatings applied to articles that come in contact with the skin. Such articles include, but are not limited to, barrier articles such as gloves, condoms, and diaphragms, as well as articles such as eye protection devices, medical drapes, protective clothing, footwear, wound dressings, devices applied to stoma (e.g., colostomy bags, tracheostomy tubes and fittings), surgical masks, etc. Examples of non-medical articles that may be coated according to the invention include, but are not limited to, gloves or rubber fingers used in the food service industry, banking industry, or gardening, athletic wear including supports and gloves, etc.

When discussing coatings according to the invention, percentages are in weight percent unless indicated otherwise. Further, such percentages refer to a coating solution used to coat the article, rather than the amount present after the coating solution has dried, unless indicated otherwise.

The term "low concentration" means that the weight percent of a zinc salt (including the zinc ion and its binding partner) is less than 2 percent, for example between about 0.05 and 2 percent, or between about 0.1 and 2 percent, or between 0.1 and 0.5 percent, or between 0.5 and 1.5 percent, or between 0.2 and 0.5 percent, or between about 0.1 and 1 percent or between about 0.5 and 2 percent. Preferably, the water-soluble salts of zinc are present in the compositions (formulations and coatings) of the present invention in a total amount (weight of all water soluble zinc salts combined) of between about 0.1 and 0.5 percent, or less than 0.3 percent, or less than or equal to 0.2 percent.

"Water soluble" zinc salts exhibit a molar solubility in water of at least 0.1 moles/liter and preferably at least 0.17 moles/liter, at 25 degrees Celsius. Water soluble zinc salts for use in these formulations include zinc acetate (molar solubility in water of 1.64 moles/l at 25 degrees Celsius), zinc butyrate (molar solubility in water of 0.4 moles/l), zinc gluconate (molar solubility in water of 0.28 moles/l), zinc glycerate (moderately water soluble), zinc glycolate (moderately water soluble), zinc formate (molar solubility in water of 0.33 moles/l at 20 degrees Celsius), zinc lactate (molar solubility in water of 0.17 moles/l), zinc picolinate (moderately water soluble), zinc propionate (molar solubility in water of 1.51 moles/l), zinc salicylate (low water solubility), zinc tartrate (moderately water soluble) and zinc undecylenate (moderately water soluble). In preferred non-limiting embodiments, the present invention provides for formulations for coating of articles comprising two or more water soluble zinc salts each having a molar solubility in water of about 0.17-1.64 moles/liter, wherein the total weight percent of all water soluble zinc salts is between about 0.1 and 0.5 percent or less than or equal to about 0.3 percent.

A "water insoluble" zinc salt, as that term is used herein, refers to a compound having a water solubility of less than 0.1 moles/liter at 25 degrees Celsius. Non-limiting examples of water insoluble zinc salts include zinc oxide, zinc stearate, zinc citrate, zinc phosphate, zinc carbonate, and zinc borate. In specific, non-limiting embodiments, the water insoluble zinc salt is present in a concentration of between about 0.05 and 0.5 weight percent or between about 0.1 and 1 weight percent.

In further specific, non-limiting embodiments, the total amount of all zinc salts, including water soluble and water insoluble salts, is between about 0.1 and 1.5 weight percent, or between about 0.1 and 1 weight percent.

The terms "prevention" or "reduction" of irritation means a decrease in objective or subjective signs of irritation in tissues exposed to medical articles coated with formulations of the invention comprising low concentrations of two or more water-soluble, organic salts of zinc of at least 50%, and more preferably by greater than 90% relative to control tissues exposed to the barrier coated with the same formulations lacking zinc salts. Irritation in this context may be evidenced by redness or other changes in coloration, inflammation or swelling, hypersensitivity, the occurrence of burning, itching or other painful stimuli, chapping, wrinkling, rash, hives or other macroscopic or microscopic changes known to those of ordinary skill in the art to be associated with irritation.

The formulations of the invention may be applied as coatings, in an article having more than one surface, so as to coat at least one surface (the entire surface or a portion thereof) of the article. As specific, non-limiting embodiments, a coating according to the invention may be applied to the inner surface of a glove or condom, or to the outer surface of a glove or condom, or to both inner and outer surfaces of a glove or condom. Different coatings may be applied to each surface. A coating may be applied over a portion of a surface, for example, but not by way of limitation, on the inner surface of one or more fingertip of a glove.

Various embodiments of the invention may comprise an emollient, such as, but not limited to, PEG 20 almond glycerides, Probutyl DB-10, Glucam P-20, Glucam E-10, Glucam P-10, Glucam E-20, Glucam P-20 distearate, Procetyl-10 (Croda), Incroquat, glycerin, propylene glycol, cetyl acetate, and acetylated lanolin alcohol, cetyl ether, myristyril ether, hydroxylated milk glycerides, polyquaternium compounds, copolymers of dimethyl dialyl ammonium chloride and acrylic acid, dipropylene glycol methyl ethers, polypropylene glycol ethers and silicon polymers. Other suitable emollients may include hydrocarbon-based emollients such as petrolatum or mineral oil, fatty ester-based emollients, such as methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, $C_{12}$-$C_{16}$ fatty alcohol lactates such as cetyl lactate and lauryl lactate, isopropyl lanolate, 2-ethylhexyl salicylate, cetyl myristate, oleyl myristate, oleyl stearate, oleyl oleate, hexyl laurate, and isohexyl laurate. Further emollients include lanolin, olive oil, cocoa butter, and shea butter.

The present invention provides for the incorporation, into formulations and coatings, of one or more emollient solvent. Preferred emollient solvents of the invention include octoxyglycerin (Sensiva®), pentylene glycol, 1,2 hexanediol and caprylyl glycol, for example, and not by way of limitation, at a concentration of up to 5 percent or up to 3 percent, such as between 0.05 and 5 percent or between 0.1 and 3 percent.

Various embodiments of the invention may comprise a stabilizing agent, such as, but not limited to, an antioxidant (which may be at a concentration of 0.2-1%), such as but not limited to vitamin C (ascorbic acid) or vitamin E (tocopherol).

The stabilizing agents surprisingly appear to remove the turbidity of the formulations, resulting in a clear product that imparts a light feel to the surface to which it is applied.

Various embodiments of the invention may comprise a thickening agent, such as but not limited to the following (at a preferred concentration of 0.6-2%): stearyl alcohol, cationic hydroxy ethyl cellulose (U Care JR30; Amerchol), hydroxy propyl methyl cellulose, hydroxy propyl cellulose (Klucel), Polyox N-60K, chitosan pyrrolidone carboxylate (Kytamer), behenyl alcohol, zinc stearate, Crodamol STS (Croda) or an emulsifying wax, such as but not limited to, Incroquat and Polawax. Other thickening and/or gelling agents suitable for incorporation into the formulations or ointments described herein include, for example, an addition polymer of acrylic acid, a resin such as Carbopol® ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, crodomol, crothix, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminum silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentonite, stearalkonium hectorite, stearyl alcohol, tallow alcohol, TEA-hydrochloride, tragacanth gum, tridecyl alcohol, trometamine magnesium aluminum silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhydride copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/glycerin/glycidyl decanoate copolymer, ophthalmic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof.

An embodiment of the invention may comprise phenoxyethanol (0.3-1.0%) as a solubilizing agent.

Various embodiments of the invention may comprise a humectant, such as but not limited to glycerin, panthenol, Glucam P20, 1-2-propylene glycol, dipropylene glycol, polyethylene glycol, 1,3-butylene glycol, or 1,2,6-hexanetriol. The concentration of humectant may be between about 0.1 and 5 percent, or between about 0.1 and 0.5 percent.

In non-limiting embodiments, coatings of the invention comprise one or more antimicrobial or preservative agent, preferably at a total concentration between 0.05 and 5 weight percent or between 0.05 and 2 weight percent or between 0.1 and 2 weight percent. Examples of preferred antimicrobial and/or preservative agents include, but are not limited to, chlorhexidine gluconate (CHG), benzalkonium chloride (BZK), or iodopropynylbutyl carbamate (IPBC; Germall plus). Further examples of antimicrobial agents include, but are not limited to, iodophors, iodine, benzoic acid, dihydroacetic acid, propionic acid, sorbic acid, methyl paraben, ethyl paraben, propyl paraben, butyl paraben, cetrimide, quaternary ammonium compounds, including but not limited to benzethonium chloride (BZT), dequalinium chloride, biguanides such as chlorhexidine (including free base and salts (see below)), PHMB (polyhexamethylene biguanide), chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylene, foscarnet, miconazole, fluconazole, itriconazole, ketoconazole, and pharmaceutically acceptable salts thereof.

Specific, non-limiting embodiments of the invention contain essentially no quaternary ammonium compound, such as but not limited to benzalkonium chloride, benzethonium chloride (BZT), and dequalinium chloride.

Pharmaceutically acceptable chlorhexidine salts that may be used as antimicrobial agents according to the invention include, but are not limited to, chlorhexidine palmitate, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate. Chlorhexidine free base is a further example of an antimicrobial agent.

These and further examples of antimicrobial agents useful in this invention can be found in such references as Goodman and Gilman's The Pharmacological Basis of Therapeutics (Goodman Gilman A, Rall T W, Nies A S, Taylor P, ed. (Pergamon Press; Elmsford, N.Y.: 1990)), the contents of which are hereby incorporated by reference.

Various embodiments of the invention may comprise a neutralizing agent to neutralize carboxyl groups present in one or more other component, such as carboxyl groups in a thickening agent. Suitable neutralizing agents include diisopropylamine and triethanolamine.

Various embodiments of the invention may comprise a surfactant. The surfactant may be an anionic surfactant, a cationic surfactant, an ampholytic surfactant, or a nonionic surfactant. Examples of nonionic surfactants include polyethoxylates, fatty alcohols (e.g., ceteth-20 (a cetyl ether of polyethylene oxide having an average of about 20 ethylene oxide units) and other "BRIJ"® nonionic surfactants available from ICI Americas, Inc. (Wilmington, Del.)), cocamidopropyl betaine, alkyl phenols, fatty acid esters of sorbitol, sorbitan, or polyoxyethylene sorbitan. Suitable anionic surfactants include ammonium lauryl sulfate and lauryl ether sulfosuccinate. Preferred surfactants include lauroyl ethylenediamine triacetic acid sodium salt at a concentration between about 0.5-2.0%, Pluronic F87 at about 2.0%, Masil SF-19 (BASF) and incromide. Suitable concentrations of surfactant are between about 0.05% and 2%. Water used in the formulations described herein is preferably deionized water having a neutral pH. Alcohols that may be used according to the invention include but are not limited to ethanol and isopropyl alcohol.

Non-limiting embodiments of the invention may comprise a silicone powder, such as, but not limited to, Dow Corning 9701 Cosmetic Powder. In specific non-limiting embodiments, the amount of such powder may be between about 0.1 and 5 percent, or between 0.2 and 1 percent.

Various embodiments of the invention may comprise additional additives, including but not limited to a silicone fluid (such as dimethicone or cyclomethicone), a silicone emulsion, dyes, fragrances, pH adjusters, including basic pH adjusters such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids (e.g., hydrochloric acid, nitric acid, phosphoric acid, sulfuric acid, citric acid, glycolic acid, and lactic acid); vitamins such as vitamin A, vitamin E and vitamin C; polyamino acids and salts, such as ethylenediamine tetraacidic acid (EDTA), preservatives such as Germall plus and DMDM hydantoin.

Various embodiments of the invention may comprise an essential oil ("EO"), which is a volatile oil obtained from a plant or an animal source that comprises one or more active agent (also referred to herein as an Isolated Component or "IC") which may be, for example but not by way of limitation, a monoterpene or sesquiterpene hydrocarbon, alcohol, ester, ether, aldehyde, ketone, or oxide. Examples of these EOs include, but are not limited to, almond oil, ylang-ylang oil, neroli oil, sandalwood oil, frankincense oil, peppermint oil, lavender oil, jasmine absolute, geranium oil bourbon, spearmint oil, clove oil, lemongrass oil, cedarwood oil, balsam oils, and tangerine oil. Alternatively, the present invention provides for the use of active agents found in essential oils (ICs) such as, but not limited to, 1-citronellol, α-amylcinnamaldehyde, lyral, geraniol, farnesol, hydroxycitronellal, isoeugenol, eugenol, eucalypus oil and eucalyptol, lemon oil, linalool, and citral. Apart from their effects as fragrances or flavorants, such compounds also may be useful in the instant invention as antimicrobial agents. The concentrations of EO or IC may be between about 0.3 and 1 percent or between about 0.1 and 0.5 percent or between 0.5 and 2 percent (all weight percent values).

Ambient temperature is defined herein between 20 and 35° C. Room temperature is defined herein between 20 and 25° C.

The invention provides for methods of using the foregoing compositions to prevent irritation to an epithelial tissue (e.g. a mucosal tissue or the skin) comprising applying an effective amount of the composition to the surface or coating an article which is intended to come into contact with the skin or a mucosal tissue. Examples of irritants against which protection may be afforded include, but are not limited to, those induced by physical, chemical, mechanical or biological irritants. Specific examples of the foregoing irritants include, but are not limited to, means for hair removal (e.g. depilatories, waxing and razors), hair relaxants (e.g. sodium hydroxide, calcium hydroxide, thioglycolates), antiperspirants (e.g aluminum chlorhydrate and other aluminium salts), dermatological treatments (e.g. alpha hydroxy acids (AHAs), especially glycolic and trichloroacetic acids), keratoyltic skin-irritating conditions (e.g. psoriasis, dandruff, etc.), infectious skin irritants (e.g. bacteria and fungi), and agents applied for therapeutic purposes. The epithelial surface to be protected from irritation may be dermal or mucosal, including vaginal, anorectal, oral or nasal.

Examples of infectious agents against which protection may be afforded include, but are not limited to, infectious agents associated with sexually transmitted diseases, including Human Immunodeficiency Virus (HIV), Human Papilloma Virus (HPV), Herpes Simplex Virus (HSV), *Chlamydia trachomatis, Neisseria gonorrhoea, Trichomonas vaginalis*, and *Candida albicans*, as well as infectious agents that may be encountered in a health care setting, including but not limited to *Staphylococcus aureus, Pseudomonas aeruginosa, Streptococcus pneumoniae, Escherichia coli, Salmonella typhimurium, Enterococcus*, and *Neisseria meningitidis*, HIV, varicella virus and Hepatitis viruses (e.g., A, B, and C).

In certain alternative non-limiting embodiments, the formulations and/or coatings of the invention lack an antimicrobial agent selected from the group consisting of iodophors, iodine, benzoic acid, dihydroacetic acid, propionic acid, sorbic acid, methyl paraben, ethyl paraben, propyl paraben, butyl paraben, cetrimide, quaternary ammonium compounds, including but not limited to benzalkonium chloride, dequalinium chloride, biguanides such as chlorhexidine (including free base and salts (see below)), chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylene, foscarnet, miconazole, fluconazole, itriconazole, ketoconazole, and pharmaceutically acceptable salts thereof.

In still further embodiments, the present invention provides for a zinc slurry that may be applied to a latex article (such as a condom or glove) to reduce or prevent irritation. The zinc slurry may comprise, for example but not by way of limitation, at least two water-soluble zinc salts (as set forth above) at a concentration of between 0.5-2%, optionally one or more water-insoluble zinc salts (as set forth above) at a concentration of 0.1-1 percent, and panthenol at a concentration of 0.1-4%. Such a slurry may be mixed with a liquid, such as a silicone fluid, in a ratio of between 1:5 to 1:10, and then applied to the surface of the article which will be in contact with the skin. In a specific embodiment nonlimiting embodiment, the present invention provides for an emulsion which may be used to coat the interior surface of a glove, such as a latex glove.

In one particular set of non-limiting embodiments, the present invention provides for a coating for application to or as applied on an article, comprising two water soluble zinc salts, each at a concentration of between 0.1 and 1 weight percent, a derivative of pantothenic acid, such as panthenol, at a concentration of between about 0.05 and 0.5 weight percent, and an antimicrobial agent as set forth above (e.g., a biguanide such as chlorhexidine), at a concentration of between about 1 and 5 weight percent. Coating solutions may further comprise a silicone emulsion at a concentration between about 70 and 95 weight percent. In certain non-limiting embodiments, said coating further comprises a third water soluble zinc salt at a concentration of between 0.1 and 1 weight percent. In certain non-limiting embodiments, in such coatings, which optionally comprise a third water soluble zinc salt, the combined amounts of all water soluble zinc salts is between about 0.1 and 2 weight percent. In certain non-limiting embodiments, such coatings comprise a silicone powder, as set forth above, at a concentration of between about 0.2 and 1 percent.

In particular non-limiting embodiments, the present invention provides for a coating formulation comprising:
(i) chlorhexidine gluconate at a concentration of between about 2 and 4 weight percent;
(ii) panthenol at a concentration of between about 0.3 and 1 weight percent;
(iii) zinc acetate at a concentration of between about 0.1 and 0.5 weight percent;
(iv) zinc lactate at a concentration of between about 0.5 and 1.5 percent;
(v) a quaternary ammonium compound at a concentration of between about 0.05 and 0.2 weight percent; and
(vi) a silicone emulsion at a concentration of between about 1 and 5 weight percent;

wherein the formulation does not comprise a water insoluble zinc salt, optionally further comprising between about 0.5 and 2 weight percent farnesol, between about 0.5 and 3 weight percent octoxyglycerin, and/or between about 0.1 and 0.5 weight percent silicone powder.

In other non-limiting embodiments, the present invention provides for a coating formulation comprising:
(i) chlorhexidine gluconate at a concentration of between about 2 and 4 weight percent;
(ii) panthenol at a concentration of between about 0.3 and 1 weight percent;
(iii) zinc acetate at a concentration of between about 0.1 and 0.5 weight percent;
(iv) zinc lactate at a concentration of between about 0.5 and 1.5 percent;
(v) zinc oxide at a concentration of between about 0.1 and 1.0 weight percent; and
(vi) a silicone emulsion at a concentration of between about 1 and 5 weight percent;

wherein the formulation does not comprise a quaternary ammonium compound, optionally further comprising between about 0.5 and 2 weight percent farnesol, between about 0.5 and 3 weight percent octoxyglycerin, and/or between about 0.1 and 0.5 weight percent silicone powder.

In yet further non-limiting embodiments, the present invention provides for a coating formulation comprising:

(i) chlorhexidine gluconate at a concentration of between about 2 and 4 weight percent;

(ii) panthenol at a concentration of between about 0.3 and 1 weight percent;

(iii) zinc acetate at a concentration of between about 0.1 and 0.5 weight percent;

(iv) zinc lactate at a concentration of between about 0.5 and 1.5 percent;

(v) a quaternary ammonium compound at a concentration of between about 0.05 and 0.2 weight percent;

(vi) a silicone emulsion at a concentration of between about 1 and 5 weight percent;

(vii) between about 0.5 and 2 weight percent farnesol;

(viii) between about 0.5 and 3 weight percent octoxyglycerin; and (ix) between about 0.1 and 0.5 weight percent silicone powder.

In non-limiting embodiments, the present invention provides for an article, especially a medical article, prepared by a method which comprises coating a surface of an uncoated article with a coating formulation as set forth above. Coating such articles would render them less irritating if contacted with skin or mucous membranes, and would render them more effective in inhibiting transmission of infectious disease.

Table 1 sets forth concentration ranges of components which may be comprised in non-limiting examples of formulations of the invention.

TABLE 1

| Constituent | Chemical Name | |
|---|---|---|
| Chlorhexidine Gluconate 20% Sol. | Soluble or Insoluable Biguanide Salt or free Base | 0.05%-10.0% |
| Water | | QS to 100% if needed |
| D Panthanol | D and/or L Panthanol | 0%-3.0% |
| Zinc Acetate, 100% | | 0%-2.0% |
| Zinc Lactate, 100% | | 0%-5.0% |
| Ucare JR30M, 100% | Polyquaternium 10 | 0%-2.0% |
| Benzethonium Chloride 100% | Quaternary Alkylaryl-Dimethylammonium Chloride Compound | 0%-3.5% |
| Zinc Gluconate, 100% | | 0.01%-5.0% |
| Phenoxyethanol, 100% | | 0%-3.0% |
| Teric N-100, 20% | Ethoxylated nonyl phenol with EO from 3-150 | 0%-10.0% |
| Detex A50, 50% | | 0%-3.0% |
| Silicone Dow Corning 939, 35% | Amenofunctional Siloxane | 0%-7.0% |
| Farnesol, 100% | Sesquiterpenoid | 0%-5.0% |
| 1,2-Octanediol, 98+% | Aliphatic and/or Aromatic and/or Cyclic glycol wit of with out double bonds and with carbon from 2-20 | 0%-10.0% |
| Hydrolite 5 | Aliphatic and/or Aromatic and/or Cyclic glycol wit of with out double bonds and with carbon from 2-20 | 0%-10.0% |
| Sensiva | Octoxyglycerin | 0%-5.0% |
| Silicone-9701 | Amorphous fumed silica | 0%-3.0% |

Table 2 sets forth concentration ranges of components which may be comprised in non-limiting examples of formulations of the invention, which do not comprise insoluble zinc salts:

TABLE 2

| CONSTITUENT | % wt/wt (Range) |
|---|---|
| Phase 1 | |
| Chlorhexidine Gluconate | 2-4 |
| Water—Deionized | 40-60 |
| D-L Panthenol | 0.3-1.0 |
| Zinc Acetate | 0.1-0.5 |
| Zinc Lactate | 0.5-1.5 |
| Ucare JR-30M | 0.1-0.3 |
| Benzethonium Chloride | 0-0.2 |
| Zinc Gluconate | 0.2-0.5 |
| Phenoxyethanol | 0.5-1.0 |
| Phase 2 | |
| Water—Deionized | 20-30 |
| Silicone—Dow Corning 939 Emulsion | 1.0-5.0 |
| Farnesol | 0.5-2.0 |
| 1,2-Octanediol | 1.0-4.0 |
| Sensiva SC-50 | 0.5-3.0 |

According to non-limiting methods of the invention, the coating formulation is prepared by first preparing two solutions (Phase 1 and Phase 2, above), which are then mixed together.

Table 3 sets forth concentration ranges of components which may be comprised in non-limiting examples of formulations of the invention, which optionally comprise insoluble zinc salts:

TABLE 3

| CONSTITUENT | % wt/wt (Range) |
|---|---|
| Phase 1 | |
| Chlorhexidine Gluconate | 2-4 |
| Water—Deionized | 40-60 |
| D-L Panthenol | 0.3-1.0 |
| Zinc Acetate | 0.1-0.5 |
| Zinc Lactate | 0.5-1.5 |
| Ucare JR-30M | 0.1-0.3 |
| Benzethonium Chloride | 0-0.2 |
| Zinc Gluconate | 0.2-0.5 |
| Zinc Oxide | 0-1.0 |
| Phenoxyethanol | 0.5-1.0 |
| Phase 2 | |
| Water—Deionized | 20-30 |
| Silicone—Dow Corning 939 Emulsion | 1.0-5.0 |
| Farnesol | 0.5-2.0 |
| 1,2-Octanediol | 1.0-4.0 |
| Sensiva SC-50 | 0.5-3.0 |

According to non-limiting methods of the invention, the coating formulation is prepared by first preparing two solutions (Phase 1 and Phase 2, above), which are then mixed together.

One specific, non-limiting embodiment of the invention is the formulation set forth below in Table 4:

TABLE 4

| CONSTITUENT | % wt/wt |
|---|---|
| Phase 1 | |
| Chlorhexidine Gluconate | 3.00 |

TABLE 4-continued

| CONSTITUENT | % wt/wt |
|---|---|
| Water—Deionized | 53.90 |
| D' Panthenol | 0.36 |
| Zinc Acetate | 0.30 |
| Zinc Lactate | 1.00 |
| Ucare JR-30M | 0.10 |
| Benzethonium Chloride | 0.20 |
| Zinc Gluconate | 0.30 |
| Phenoxyethanol | 0.55 |
| SUBTOTAL: | 59.71 |
| Phase 2 | |
| Water—Deionized | 27.36 |
| Teric N-100 | 1.90 |
| Cetrimonium Chloride | 0.03 |
| Silicone—Dow Corning 939 Emulsion | 2.50 |
| Farnesol | 1.00 |
| 1,2-Octanediol | 3.25 |
| Pentylene Glycol | 3.00 |
| Sensiva SC-50 | 1.00 |
| Silicone—Dow Corning 9701 Cosmetic Powder | 0.25 |
| SUBTOTAL: | 40.29 |
| TOTAL: | 100.00 |

Various publications are cited herein, the contents of which are hereby incorporated by reference in their entireties.

We claim:

1. A coating formulation comprising:
   (i) chlorhexidine gluconate at a concentration of between about 2 and 4 weight percent;
   (ii) panthenol at a concentration of between about 0.3 and 1 weight percent;
   (iii) zinc acetate at a concentration of between about 0.1 and 0.5 weight percent;
   (iv) zinc lactate at a concentration of between about 0.5 and 1.5 percent;
   (v) zinc oxide at a concentration of between about 0.1 and 1.0 weight percent; and
   (vi) a silicone solution consisting essentially of:
      (a) a silicone emulsion at a concentration of between about 1 and 5 weight percent;
      (b) an octanediol compound at a concentration of between 1 and 4 weight percent;
      (c) farnesol at a concentration of between 0.5 and 2 weigh percent; and
   (d) octoxyglycerin at a concentration of between about 0.5 and 3 weight percent,
   wherein the formulation does not comprise a quaternary ammonium compound.

2. A coating formulation comprising:
   chlorhexidine gluconate at a concentration of between about 2 and 4 weight percent;
   (ii) panthenol at a concentration of between about 0.3 and 1 weight percent;
   (iii) zinc acetate at a concentration of between about 0.1 and 0.5 weight percent;
   (iv) zinc lactate at a concentration of between about 0.5 and 1.5 percent;
   (v) a quaternary ammonium compound at a concentration of between about 0.05 and 0.2 weight percent; and
   (vi) a silicone solution consisting essentially of:
      (a) a silicone emulsion at a concentration of between about 1 and 5 weight percent;
      (b) between about 0.5 and 2 weight percent farnesol;
      (c) between about 0.5 and 3 weight percent octoxyglycerin; and
      (d) an octanediol compound at a concentration of between 1 and 4 weight percent.

3. An article prepared by a method which comprises coating a surface of an uncoated article with the coating formulation of claim 1.

4. An article prepared by a method which comprises coating a surface of an uncoated article with the coating formulation of claim 2.

* * * * *